United States Patent
Liu et al.

(10) Patent No.: US 10,286,117 B2
(45) Date of Patent: May 14, 2019

(54) TITANIUM NAIL CAPABLE OF LOADING DRUG AND DRUG-LOADED TITANIUM NAIL AND PREPARING METHOD OF THE SAME

(71) Applicant: B.J. ZH. F. PANTHER MEDICAL EQUIPMENT CO. LTD., Beijing (CN)

(72) Inventors: Qing Liu, Beijing (CN); Cong Pu, Beijing (CN)

(73) Assignee: B.J. ZH. F. PANTHER MEDICAL EQUIPMENT CO. LTD., Beijing (CN)

( * ) Notice: Subject to any disclaimer, the term of this patent is extended or adjusted under 35 U.S.C. 154(b) by 157 days.

(21) Appl. No.: 15/504,318

(22) PCT Filed: Dec. 9, 2016

(86) PCT No.: PCT/CN2016/109120
§ 371 (c)(1),
(2) Date: Feb. 16, 2017

(87) PCT Pub. No.: WO2018/032664
PCT Pub. Date: Feb. 22, 2018

(65) Prior Publication Data
US 2018/0221543 A1 Aug. 9, 2018

(30) Foreign Application Priority Data

Aug. 19, 2016 (CN) .......................... 2016 1 0694731

(51) Int. Cl.
| | | |
|---|---|---|
| A61L 33/02 | (2006.01) |
| A61L 31/02 | (2006.01) |
| A61L 31/08 | (2006.01) |
| A61L 31/14 | (2006.01) |
| A61L 31/16 | (2006.01) |
| A61K 9/00 | (2006.01) |

(52) U.S. Cl.
CPC .......... *A61L 31/022* (2013.01); *A61K 9/0024* (2013.01); *A61L 31/088* (2013.01); *A61L 31/146* (2013.01); *A61L 31/16* (2013.01); *A61L 2300/104* (2013.01); *A61L 2300/414* (2013.01); *A61L 2300/602* (2013.01); *A61L 2300/606* (2013.01); *A61L 2300/622* (2013.01); *A61L 2400/08* (2013.01)

(58) Field of Classification Search
CPC ........ A61L 31/00; A61L 31/02; A61L 31/022; A61L 31/043; A61L 31/08; A61L 31/14; A61L 31/146
See application file for complete search history.

(56) References Cited

U.S. PATENT DOCUMENTS

| | | | | |
|---|---|---|---|---|
| 2002/0198601 A1* | 12/2002 | Bales | .................... | A61B 17/80 623/23.55 |
| 2007/0259101 A1 | 11/2007 | Kleiner et al. | | |
| 2013/0164346 A1* | 6/2013 | Lee | ........................ | A61K 47/02 424/400 |
| 2015/0209474 A1 | 7/2015 | Haugen et al. | | |

FOREIGN PATENT DOCUMENTS

| | | |
|---|---|---|
| CN | 1762330 A | 4/2006 |
| CN | 101327343 A | 12/2008 |
| CN | 101461943 A | 6/2009 |
| CN | 101905040 A | 12/2010 |
| CN | 102028973 A | 4/2011 |
| CN | 102196826 A | 9/2011 |
| CN | 102266596 A | 12/2011 |
| CN | 102631714 A | 8/2012 |
| CN | 105326535 A | 2/2016 |
| CN | 105457104 A | 4/2016 |
| WO | 2008064904 A1 | 6/2008 |

OTHER PUBLICATIONS

Wenping Chen, Hong-bing Zhan, Recent developments of drug eluting stent coatings, Acta Phamiaceutica Sinica Nov. 30, 2011, 46 (11): 1301-1307.

* cited by examiner

*Primary Examiner* — Micah Paul Young
(74) *Attorney, Agent, or Firm* — Gokalp Bayramoglu

(57) ABSTRACT

The present invention discloses a preparation method of a titanium nail capable of loading a drug. The titanium nail capable of loading a drug includes a titanium nail body capable of loading a drug, and a microporous ceramic layer capable of loading a drug arranged on the surface of the titanium nail body. The steps of the method include: pretreating the surface of the titanium nail body, preparing a microporous mould for hyaluronic acid-alginic acid microspheres, preparing a titanium sol solution, coating film, pore-forming and calcining. It fails to generate the exfoliations and the wear debris to prevent the human body from "wear debris disease" and reaction to a foreign body. Moreover, various drugs such as the antibacterial drugs, and the drugs for promoting the healing etc. can be loaded, targeted and slow-released, which is good for medical usage.

14 Claims, No Drawings

TITANIUM NAIL CAPABLE OF LOADING DRUG AND DRUG-LOADED TITANIUM NAIL AND PREPARING METHOD OF THE SAME

CROSS REFERENCE TO RELATED APPLICATIONS

This application is the national phase entry of International Application No. PCT/CN2016/109120, filed on Dec. 9, 2016, which is based upon and claims priority to Chinese Patent Application No. 201610694731.X, filed on Aug. 19, 2016, the entire contents of which are incorporated herein by reference.

TECHNICAL FIELD

The present invention relates to the technical field of microporous drug-loading, particularly relating to a titanium nail capable of loading a drug and a drug-loaded titanium nail and a preparation method thereof.

BACKGROUND

A pure titanium stapler (suturing device) is a common surgical instrument for suturing the digestive tract, the respiratory tract, and the skin and mucosa after a surgery recently, and belongs to a category of surgical implants. The ideal biological material, like a surgical implant, should be a special functional material that when in direct contact with or acting on human tissues, body fluid or blood, or otherwise interacting with body; should have no toxic side effects on the human body. The ideal biological material also has no hemolysis, direct or indirect infection, human cell mutation, aberration, carcinogenesis, immune rejection, and allergic reaction when in direct contact with or acting on human tissues, body fluid or blood, or otherwise acting with the body. At present, the most commonly used materials are medical metal material, medical natural polymer material, medical synthetic polymer material, and medical ceramics, etc. In particular, medical metal material is the most widely used in clinical applications nowadays, due to the advantages of great compatibility and a wide range of adaptation with the human body. However, this kind of medical implant material has a common deficiency, i.e., the wear debris generated due to wear, would cause toxicity, immune reaction, allergic reaction, and even form tumors locally. On the other hand, when suturing the trauma tissues it is likely for the stapler (suturing device) of the digestive tract, the respiratory tract, and the skin and mucosa to penetrate the numerous blood vessels under the surface of the tissues where various pathogenic bacteria and non-pathogenic bacteria are usually parasitized in the tissue surface, easily causing a secondary infection. In order to correct the deficiencies above, researchers attempt to use a polymer compound as the adhesive agent and drug-loaded layer, however this approach causes new problems. The adhesive agent and drug-loaded layer are made of a polymer compound. First, there is the issue of adding new substances that need to be metabolized in the human body. Secondly, the drug-loaded polymer layer and the surface of the metal implant peel and shed at different degrees, and the debris thereof enters into the blood vessels, causing adverse reactions such as an acute and sub-acute thrombosis, an infection and a rejection in the patient.

As to the defects of the prior art, the objective of the present invention is to provide a new type of titanium nail capable of loading a drug and a preparation method thereof, as a carrier for loading a drug, as well as overcoming the deficiencies and defects mentioned above.

SUMMARY OF THE INVENTION

The technical problem that the present invention aims to solve is to provide a preparation method for a titanium nail capable of loading a drug, making the obtained drug loading layer not only fail to generate exfoliation, but also have a slow-releasing function, overcoming the deficiencies of the existing stapler (suturing device) titanium nail.

In order to solve the technical problem as above, the present invention provides a preparation method of a titanium nail capable of loading a drug. The titanium nail capable of loading a drug includes a titanium nail body, and a microporous ceramic layer capable of loading a drug arranged on the surface of the titanium nail body. The preparation method of the titanium nail capable of loading at drug comprises:

(1) Pretreating: treating the surface of the titanium nail body by a heated alkaline solution, then drying after repeated cleanings;

(2) Preparing hyaluronic acid-alginic acid microspheres: weighing equal amounts of sodium hyaluronate and sodium alginate and putting into the high speed vacuum homogenizer; adding deionized water and calcium chloride solution sequentially, vacuum homogenizing under a strong agitation; then adding ethanol and continuing to agitate to generate a deposit of the hyaluronic acid-alginic acid microspheres; washing with anhydrous ethanol; vacuum freeze drying; then suspending the product in the anhydrous ethanol solution;

(3) Preparing titanium sol solution: dissolving tetrabutyl titanate in the ethanol; adding sodium alginate solution and acetylacetone sequentially when agitating; continuing to agitate to generate the stable and uniform titanium sol solution; and aging at the room temperature.

(4) Coating and pore-forming mixing the ethanol suspension of the hyaluronic acid-alginic acid microspheres obtained from step (2) with the titanium sol solution obtained from step (3); then coating on the surface of the titanium nail body with the mixed solution and drying to obtain a coated titanium nail; Next, heat treating the coated titanium nail in hot water; with the hyaluronic acid and the alginic acid dissolving and stripping in the hot water, forming a microporous titanium dioxide film on a surface of the coated titanium nail.

(5) Calcining: calcining the titanium nail coated with the titanium dioxide film obtained from step (4) in a calcinator to form a titanium nail having a microporous titanium dioxide ceramic layer; water washing and drying to obtain the titanium nail capable of loading a drug.

Furthermore, step (2) specifically is provided as below. 10-30 g of sodium hyaluronate and sodium alginate are weighed with equal amounts, and are both put into a high speed vacuum homogenizer. Deionized water is added to dissolve them. 100-30 ml of calcium chloride solution at a concentration of 1% to 3% is then added and vacuum homogenized under strong agitation. The ethanol with three times volume than that of the mixture solution of the calcium chloride solution, the sodium hyaluronate and the sodium alginate is then added and agitated continually to generate a deposit of the hyaluronic acid-alginic acid microspheres, which is washed three times using anhydrous ethanol and vacuum freeze dried and then suspended in the anhydrous ethanol solution. A viscosity-average molecular weight of the sodium hyaluronate is 800-1500 thousand Dalton. A diameter of the formed hyaluronic acid-alginic acid microsphere is 5-10 um.

Furthermore, step (3) specifically is provided as below 50-100 ml of the tetrabutyl titanate is measured and dissolved in 1000 ml of the anhydrous ethanol. 100-200 ml of the 1% sodium alginate solution is slowly added when agitating. Next, 3-6 ml of acetylacetone is added and agitated continually at the room temperature to generate the titanium sol solution, which is aged at the room temperature for 24 hours.

Furthermore, step (4) specifically is provided as below. The ethanol suspension of the hyaluronic acid-alginic acid microspheres obtained from step (2) is mixed with the titanium sol solution obtained from step (3) in a proportion of 2-4.5:3, and agitated. Next, the mixed solution is coated on the surface of the titanium nail body using a method of salivation method. A thickness of the coating film is 10-15 um. Drying is conducted at 90° C. to obtain the coated titanium nail. Next, the coated titanium nail is heat treated in the hot water at 95-98° C. With the hyaluronic acid and the alginic acid dissolving and stripping in the hot water, a macroporous titanium dioxide film is formed on the surface of the coated titanium nail.

Furthermore, the heated alkaline solution in step (1) is NaOH solution having a temperature of 70-90° C., and a concentration of 2-5 mol/L. The titanium nail body is heat preserved for 24-48 hours in the NaOH solution. A calcining condition in the calcinator of step (5) is that the temperature is raised at a constant rate of 2° C./min. Heat preservation is conducted for 3-5 hours after the temperature reaches 300-500° C.

The present invention also provides a titanium nail capable of loading a drug made by the preparation method of the titanium nail capable of loading a drug. A plurality of micropores having an average pore diameter of 0.5-6.5 um and connected with each other, are arranged uniformly in the titanium dioxide ceramic layer.

The present invention further provides a method for preparing a drug-loaded titanium nail with the titanium nail capable of loading a drug. The method includes the following steps: putting the titanium nail capable of loading a drug into a vacuum device; importing the drugs to be loaded, which are dissolved in a volatile organic solvent, in a vacuum condition; extracting the titanium nail and putting into an another vacuum device to be dried under vacuum. The method is a preparation method of drug-loaded titanium nail for the drugs easily soluble in the organic solvents. The obtained drug-loaded titanium nail is a drug-loaded titanium nail loaded with sulfadiazine or silver sulfadiazine; or a drug-loaded titanium nail loaded with growth factors.

Additionally, the present invention further provides a method of preparing a drug-loaded titanium nail with the titanium nail capable of loading a drug. The method includes the following steps: putting the titanium nail capable of loading a drug in a vacuum device; importing a solution of the drug to be loaded in a vacuum condition; extracting the titanium nail and put into a vacuum freeze dryer to be dried. The method is a preparation method of drug-loaded titanium nail for the drugs insoluble in the organic solvents. The obtained drug-loaded titanium nail is a titanium nail loaded with various growth promoting factors for human tissue cells.

With the technical solution above, the present invention has at least the following advantages:

In the present invention, with the microporous ceramic layer on the surface of the stapler (suturing device) titanium nail body, it is hard for the metal ions on the surface of the titanium nail to penetrate or leach/seep into the human body. The ceramic's corrosion resistance and wear resistance prevents the metal ions from penetrating or leaching/seeping into the body. Further, it fails to generate the exfoliations and the wear debris to prevent human body from generating "wear debris disease" and a foreign body. Moreover, various drugs such as the antibacterial drugs, and the drugs for promoting the healing etc. can be loaded, targeted and slow-released, which is good for medical usage.

DETAILED DESCRIPTION OF THE INVENTION

As to the deficiencies of the prior art, the present invention provides a titanium nail capable of loading a drug having a microporous ceramic layer formed on the surface of the stapler (suturing device) titanium nail. The microporous ceramic layer is prepared on the surface of the pure titanium stapler (suturing device) nail as a carrier for drugs, not only slow-releasing drugs, but also preventing the exudation of metal ions, so as to overcome the deficiencies and defects of the existing titanium nails. The material of the stapler (suturing device) titanium nail of the invention is pure titanium, which is a medical material that meets the requirements of the national standard for the medical usage. The material can be used to prepare various types of staplers (suturing devices) for use in surgical operations of the digestive tract, the respiratory tract, and the skin and mucosa. The specific structure and the preparation method of the titanium nail capable of loading a drug of the present invention are described as below:

The titanium nail capable of loading a drug of the present invention includes a titanium nail body, and a microporous ceramic layer capable of loading a drug arranged on a surface of the titanium nail body. The microporous ceramic layer capable of loading a drug is a microporous titanium dioxide ceramic layer formed by calcining in a calcinator. The micropores of the titanium dioxide ceramic layer are arranged uniformly having an average pore diameter of 0.5-0.6 um. The microporous titanium dioxide ceramic layer with such diameter can increase the surface area of the stapler (suturing device) titanium nail, work as a storage space for drugs when loading a drug, and make drugs stably and uniformly distributed in the micropores on the surface of the stapler (suturing device) titanium nail.

A drug-loaded titanium nail is obtained by importing the drugs to be loaded into the titanium nail capable of loading a drug in a vacuum condition. The drug imported into the drug-loaded titanium nail may be sulfadiazine or silver sulfadiazine dissolved in a concentrated ammonia solution, or growth factors dissolved in ether solution, or various growth promoting factors for human tissue cells, etc. Under the action of the stapler (suturing device), this drug-loaded titanium nail can have targeting effects on a tissue, and release drugs slowly in the tissue in a targeted manner, so as to play a role in bacteriostasis and promoting the healing, etc.

The preparation method of the titanium nail capable of loading a drug of the present invention includes the following steps:

(1) Pretreating: the surface of the titanium nail body is treated to remove impurities, such as oil and an oxide film, on the surface of the titanium nail body, using a heated NaOH solution. The titanium nail is then washed repeatedly in an ultrasonic wave with deionized water and dried. The other alkaline solutions, such as KOH solution, etc., may be used to treat the surface of the titanium nail body as well.

(2) Preparing a hyaluronic acid-alginic acid microsphere: at room temperature, equivalent amounts of sodium hyaluronate and sodium alginate are weighed and put into a high speed vacuum homogenizer. The deionized water and calcium chloride solution are added sequentially and vacuum homogenized under a strong agitation. The ethanol is then added and agitated continually to generate a deposit of the hyaluronic acid-alginic acid microspheres having a diameter of 5-10 um. The microspheres are washed with anhydrous ethanol, vacuum freeze dried and then suspended in the anhydrous ethanol solution.

(3) Preparing a titanium sol solution: at room temperature, tetrabutyl titanate is dissolved in ethanol. The sodium alginate solution and acetylacetone are added sequentially when agitating, and then agitated continually to generate the stable and uniform titanium sol solution, which is then aged at room temperature for 24 hours.

(4) Coating and pore-forming: at room temperature, the ethanol suspension of the hyaluronic acid-alginic acid microspheres from step (2) is mixed with the titanium sol solution obtained from step (3). The mixed solution is then coated on the surface of the titanium nail body, and then dried. Next, the coated titanium nail is heat treated in the hot water. With the hyaluronic acid and the alginic acid dissolving and stripping in the hot water, a microporous titanium dioxide film is formed on the surface of the coated titanium nail.

(5) Calcining: the titanium nail coated with the titanium dioxide film obtained from step (4) is roasted in a calcinator to generate a titanium nail having a microporous titanium dioxide ceramic layer. The titanium nail is washed in water and dried to obtain the titanium nail capable of loading a drug.

On the basis of the preparation method of the titanium nail capable of loading a drug, the preparation method of the drug-loaded titanium nail includes the following steps:

At room temperature, the titanium nail having a microporous ceramic layer on the surface is put into the vacuum device. The organic solution prepared by volatile organic solvents and the drug to be loaded, is imported under the vacuum condition. The titanium nail is put into an another vacuum device to be dried under vacuum.

If the drug to be loaded is insoluble in volatile organic solvents, the titanium nail having the microporous ceramic layer on the surface is put into the vacuum device. The drug solution is directly imported under vacuum. The titanium nail is then put into a vacuum freeze dryer to be dried.

The theory of the titanium nail capable of loading a drug of the present invention is provided as below: First, the generation principle of the titanium sol solution should be known. Tetra-n-butyl titanate is hydrolyzed with water in the medium of ethanol solution to generate the titanium sol solution $Ti(OH)_4$, the total reaction equation thereof is: $Ti(OC_4H_9)+4H_2O = Ti(OH)_4+C_4H_9OH$. After the titanium sol solution $Ti(OH)_4$ is coated on the surface of the titanium nail body, the complete titanium dioxide film with fine pores are generated in the water solution having a temperature over 96° C. However, those fine pores having a pore diameter no more than dozens of nanometers, which is not enough to load drugs. While the calcium chloride is added into the hyaluronic acid-alginic acid solution to generate the gel, which is put in the ethanol having three times volume than that of the mixture solution of the calcium chloride solution, the sodium hyaluronate and the sodium alginate to generate micropores having a diameter of 5-10 um under a strong agitation. The microspheres are added into the titanium sol solution to work as a mould for coating and pore-forming. The titanium nail after coating is put in hot water having a temperature over 95° C., the calcium chloride separate out first, and then the hyaluronic acid-alginic acid gel depolymerizes, dissolves and snips to generate the microspheres having a diameter of 5-10 um, which are arranged uniformly on the coating film. The alginic acid is not only involved in generating spheres and pores, but also used to increase the adhesion of the titanium sol solution. Furthermore, it works with acetyl acetone to slow down the violent hydrolysis of the tetra-n-butyl titanate.

Furthermore, the study also confirmed that, under the function of hot water having a temperature of 95-98° C., in the titanium sol film on the surface of the titanium nail, microporous structures are generated due to dissolving and stripping of the hyaluronic acid-alginic acid microspheres, so as to cause the uniform nucleation and growth of the anatase type titanium dioxide in the film and thus generate the film having the anatase type titanium dioxide. Because under the action of lights, the anatase type titanium dioxide has a degradation function to organics such as drugs, etc., and thus a firm rutile type microporous titanium dioxide ceramic layer having a strong adhesion ability is converted from the anatase type titanium dioxide film on the surface of the titanium nail by calcining at a high temperature. The photocatalysis of the rutile type titanium dioxide ceramic layer is weaker than that of the anatase type titanium dioxide film. In a certain degree, the degradation of the loaded drugs in the micropores of the ceramic layer can be avoided.

The related study of the present invention also confirmed that, the microporous structure generated by dissolving and shipping of the hyaluronic acid-alginic acid microspheres has a certain degree of shrinkage in hot water and the calcining process. Thus, the micropores finally generated in the titanium dioxide ceramic layer on the surface of the titanium nail body having a pore diameter of 0.5-6.5 um.

The characteristics of the present invention are that the basic properties and performance of the titanium nail body remain unchanged, and the used reagents have no side effects on human body. Through the strict control of the molecular weight of the hyaluronic acid, the concentrations of the hyaluronic acid, the alginic acid and the calcium chloride, the additional amount of the anhydrous ethanol, the agitation speed, reaction time etc., the size and number of the micropores in the titanium dioxide ceramic layer on the surface of the titanium nail body are indirectly controlled. The antibiotics, growth promoting factors, etc. used in clinic have a molecular weight mostly of several hundred nanometers. A certain dose of drugs can be certainly loaded with the pore diameter of the micropores in the titanium dioxide ceramic layer on the surface of the titanium nail body. The existence of the micropores in the titanium dioxide ceramic layer on the surface of the titanium nail body increases the surface area and space of the titanium nail body for loading a drug accordingly. First, the drugs are relatively firmly adhered to the ceramic layer. Secondly, since the arrangement of the micropores is uniform, which makes the drugs release uniformly in a targeted manner in the tissue around the titanium nail. Since most of micropores are connected with each other, and thus have a function of slow-releasing.

The invention of preparing the titanium nail capable of loading a drug takes the preparation of the stapler (suturing device) titanium nails as an example. The detailed description of embodiments are as below:

Embodiment 1

(1) Pretreating

Several (n) stapler (suturing device) titanium nails are ultrasonically cleaned in the deionized water to remove the surface attachments. The titanium nails are put into 1000 ml of NaOH solution having a concentration of 2 mol/L and heat preserved for 24 hours at 80° C. for removing the impurities and natural oxide layers on the surface. The ultrasonic cleanings are then repeated using deionized water. Drying is conducted.

(2) Preparing Hyaluronic Acid-Alginic Acid Microspheres

At room temperature, 10 g of sodium hyaluronate and 10 g of sodium alginate are weighed separately, having a viscosity average molecular weight of 1500 thousand Dalton. Both of them are put into the high speed vacuum homogenizer. 1000 ml of deionized water is added to dissolve them. Next, 300 ml of calcium chloride solution having a concentration of is added. Vacuum homogenizing is conducted under the strong agitation. Then ethanol having three times volume than that of the mixture solution of the calcium chloride solution, the sodium hyaluronate and the sodium alginate is added. The agitation is continued to generate a deposit of the hyaluronic acid-alginic acid microspheres (that is the mould for preparing micropores). Washing is conducted three times using anhydrous ethanol. Freeze vacuum drying is conducted. Next, the microspheres are suspended in the 1000 ml of anhydrous ethanol solution. A diameter of the hyaluronic acid-alginic acid microspheres is 5-10 um.

(3) Preparing a Titanium Sol Solution

At room temperature, 50 ml tetrabutyl titanate is measured and dissolved in 1000 ml of anhydrous ethanol. Under the agitation, 100 ml of the 1% sodium alginate solution is slowly added. Next, 3 ml of acetylacetone is added. The agitation continues at the room temperature and the stable and uniform titanium sol solution is generated after 30 minutes. Aging is conducted at room temperature for 24 hours.

(4) Coating and Pore-Forming

At room temperature, the aged titanium sol solution is mixed with the ethanol suspension of the hyaluronic acid-alginic acid microspheres having a volume which is ⅔ times that of the aged titanium sol solution. The mixture is coated on the surface of the stapler (suturing device) titanium nail body using a salivation method. A thickness of the coating film is controlled to about 10-15 um.

The coated stapler (suturing device) titanium nails are dried at 90° C. Next, the stapler (suturing device) titanium nails are heat treated in hot water of 98° C. for 5 hours. With the hyaluronic acid and the alginic acid dissolved and stripped entirely in the hot water, a microporous titanium dioxide film having a pore diameter of 5-10 um, is generated on the surface of the coated titanium nails.

(5) Calcining

The coated stapler (suturing device) titanium nails are roasted in a calcinator, with the temperature raised at a constant rate of 2° C./min. Heat preservation is conducted for 3 hours after the temperature reaches 500° C. The titanium nails are extracted after natural cooling, and a fine microporous titanium dioxide ceramic layer is generated on the surface of the stapler (suturing device) titanium nails. Washing in water and drying are conducted. A thickness of the ceramic layer is 5-10 um. The micropores are arranged uniformly, having a pore diameter of 0.5-6.5 um. Some micropores are connected with each other.

Embodiment 2

(1) Pretreating

Several (n) stapler (suturing device) titanium nails are ultrasonically cleaned in the deionized water to remove the surface attachments. The titanium nails are put into 1000 ml of NaOH solution having a concentration of 5 mol/L and heat preserved for 48 hours at 70° C. for removing the impurities and natural oxide layers on the surface. The ultrasonic cleanings are then repeated using deionized water. Drying is conducted.

(2) Preparing a Hyaluronic Acid-Alginic Acid Microsphere

At room temperature, 20 g of sodium hyaluronate and 20 g of sodium alginate are weighed separately, having a viscosity average molecular weight of 1500 thousand Dalton. Both of them are put into the high speed vacuum homogenizer. 1000 ml of deionized water is added to dissolve them. Next, 200 ml of calcium chloride solution having a concentration of 2% is added. Vacuum homogenizing is conducted under the strong agitation. Then ethanol having three times volume (3600 ml) than that of the mixture solution of the calcium chloride solution, the sodium hyaluronate and the sodium alginate is added. The agitation is continued to generate a deposit of the hyaluronic acid-alginic acid microspheres (that is the mould for preparing micropores). Washing is conducted three times using anhydrous ethanol. Freeze vacuum is conducted. Next, the microspheres are suspended in the 1000 ml of anhydrous ethanol solution. A diameter of the hyaluronic acid-alginic acid microsphere is 5-10 um.

(3) Preparing a Titanium Sol Solution

At room temperature, 50 ml of tetrabutyl titanate is measured and dissolved in 1000 ml anhydrous ethanol. Under the agitation, 100 ml of the 1% sodium alginate solution is slowly added. Next, 3 ml of acetylacetone is added. The agitation continues at room temperature and the stable and uniform titanium sol solution is generated after 30 minutes. Aging is conducted at the room temperature for 24 hours.

(4) Coating and Pore-Forming

At room temperature, the aged titanium sol solution is mixed with the ethanol suspension of the hyaluronic acid-alginic acid microspheres having a volume the same as that of the aged titanium sol solution. The mixture is coated on the surface of the stapler (suturing device) titanium nail body using a salivation method. A thickness of the coating film is controlled to about 10-15 um.

The coated stapler (suturing device) titanium nails are dried at 90° C. Next, the stapler (suturing device) titanium nails are heat treated in hot water of 98° C. for 5 hors. With the hyaluronic acid and the alginic acid dissolved and stripped entirely in the hot water, a microporous titanium dioxide film having a pore diameter of 5-10 um, is generated on the surface of the coated titanium nails.

(5) Calcining

The coated stapler (suturing device) titanium nails are roasted in a calcinator, with the temperature raised at a constant rate of 2° C./min. Heat preservation is conducted for 3 hours after the temperature reaches 500° C. The titanium nails are extracted after natural cooling, and a film microporous titanium dioxide ceramic layer is generated on the surface of the stapler (suturing device) titanium nails. Washing in water and drying are conducted. A thickness of the ceramic layer is 5-10 um. The micropores are arranged uniformly, having a pore diameter of 0.5-6.5 um. Some micropores are connected with each other.

Embodiment 3

(1) Pretreating

Several (n) stapler (suturing device) titanium nails are ultrasonically cleaned in the deionized water to remove the surface attachments. The titanium nails are put into 1000 ml of NaOH solution with 5 mol/L and heat preserved for 24 hours at 90° C. for removing the impurities and natural oxide layers on the surface. The ultrasonic cleanings are then repeated using deionized water. Drying is conducted.

(2) Preparing a Hyaluronic Acid-Alginic Acid Microsphere

At room temperature, 10 g of sodium hyaluronate and 10 g of sodium alginate are weighed separately, having a viscosity average molecular weight of 800 thousand Dalton. Both of them are put into the high speed vacuum homogenizer. 1000 ml of deionized water is added to dissolve them. Next, 300 ml of calcium chloride solution having a concentration of 1% is added. Vacuum homogenizing is conducted under the strong agitation. Then ethanol having three times volume than that of the mixture solution of the calcium chloride solution, the sodium hyaluronate and the sodium alginate is added. The agitation is continued to generate a deposit of the hyaluronic acid-alginic acid microspheres (that is the mould for preparing micropores). Washing is conducted three times using anhydrous ethanol. Freeze vacuum drying is conducted. Next, the microspheres are suspended in the 1000 ml of anhydrous ethanol solution. A diameter of the hyaluronic acid-alginic acid microsphere is 5-10 um.

(3) Preparing a Titanium Sol Solution

At room temperature, 50 ml of tetrabutyl titanate is measured and dissolved in 1000 ml of anhydrous ethanol. Under the agitation, 100 ml of the 1% sodium alginate solution is slowly added. Next, 3 ml of acetylacetone is added. The agitation continues at the room temperature and the stable and uniform titanium sol solution is generated after 30 minutes. Aging is conducted at the room temperature for 24 hours.

(4) Coating and Pore-Forming

At room temperature, the aged titanium sol solution is mixed with the ethanol suspension of the Hyaluronic acid-alginic acid microspheres having a volume the same as that of the aged titanium sol solution. The mixture is coated on the surface of the stapler (suturing device) titanium nail body using a salivation method. A thickness of the coating film is controlled to about 10-15 um.

The coated stapler (suturing device) titanium nails are dried at 90° C. Next, the stapler (suturing device) titanium nail are heat treated in the hot water of 98° C. for 5 hours. With the hyaluronic acid and the alginic acid dissolved and stripped entirely in the hot water, a microporous titanium dioxide film having a pore diameter of 5-10 um, is generated on the surface of the coated titanium trails.

(5) Calcining

The coated stapler (suturing device) titanium nails are roasted in a calcinator, with the temperature raised at a constant rate of 2° C./min. Beat preservation is conducted for 3 hours after the temperature reaches 500° C. The titanium nails are extracted after natural cooling, and a film microporous titanium dioxide ceramic layer is generated on the surface of the stapler (suturing device) titanium nails. Washing in water and drying are conducted. A thickness of the ceramic layer is 5-10 um. The micropores are arranged uniformly, having a pore diameter of 0.5-6.5 um. Some micropores are connected with each other.

Embodiment 4

(1) Pretreating

Several (n) stapler (suturing device) titanium nails are ultrasonically cleaned in the deionized water to remove the surface attachments. The titanium nails are put into 1000 ml of NaOH solution having a concentration of 3.5 mol/L. The product is heat preserved for 24 hours at 80° C. for removing the impurities and natural oxide layers on the surface. The ultrasonic cleanings are then repeated using deionized water. Drying is conducted.

(2) Preparing a Hyaluronic Acid-Alginic Acid Microsphere

At room temperature, 20 g of sodium hyaluronate and 20 g of sodium alginate are weighed separately, having a viscosity average molecular weight of 800 thousand Dalton. Both of them are put into the high speed vacuum homogenizer. 1000 ml of deionized water is added to dissolve them. Next, 200 ml of calcium chloride solution having a concentration of 2% is added. Vacuum homogenizing is conducted under the strong agitation. Then ethanol having three times volume than that of the mixture solution of the calcium chloride solution, the sodium hyaluronate and the sodium alginate is added. The agitation is continued to generate a deposit of the hyaluronic acid-alginic acid microspheres (that is the mould for preparing micropores). Washing is conducted three times using anhydrous ethanol. Freeze vacuum drying is conducted. Next, the microspheres are suspended in the 1000 ml of anhydrous ethanol solution. A diameter of the hyaluronic acid-alginic acid microsphere is 5-10 um.

(3) Preparing a Titanium Sol Solution

At room temperature, 50 ml of tetrabutyl titanate is measured and dissolved in 1000 ml of anhydrous ethanol. Under the agitation, 100 ml of the 1% sodium alginate solution is slowly added. Next, 3 ml of acetylacetone is added. The agitation continues at room temperature and the stable and uniform titanium sol solution is generated after 30 minutes. Aging is conducted at room temperature for 24 hours.

(4) Coating and Pore-Forming

At room temperature, the aged titanium sol solution is mixed with the ethanol suspension of the hyaluronic acid-alginic acid microspheres, having a volume which is 1.5 times that of the aged titanium sol solution. The mixture is coated on the surface of the stapler (suturing device) titanium nail body using a salivation method. A thickness of the coating film is controlled to about 10-15 um.

The coated stapler (suturing device) titanium nails are dried at 90° C. Next, the stapler (suturing device) titanium nail are heat treated in hot water of 98° C. for 5 hours. With the hyaluronic acid and the alginic acid dissolved and stripped entirely in the hot water, a microporous titanium dioxide film having a pore diameter of 5-10 um, is generated on the surface of the coated titanium nails.

(5) Calcining

The coating stapler (suturing device) titanium nails are roasted in a calcinator, with the temperature raised at a constant rate of 2° C./min. Heat preservation is conducted for 3 hours after the temperature reaches 500° C. The titanium nails are extracted after natural cooling, and a firm microporous titanium dioxide ceramic layer is generated on the surface of the stapler (suturing device) titanium nails. Washing in water and drying are conducted. A thickness of the ceramic layer is 5-10 um. The micropores are arranged uniformly, having a pore diameter of 0.5-6.5 um. Some micropores are connected with each other.

Embodiment 5

(1) Pretreating

Several (n) stapler (suturing device) titanium nails are ultrasonically cleaned in the deionized water to remove the surface attachments. The titanium nails are put into 1000 ml of NaOH solution having a concentration of 5 mol/L. The titanium nails are heat preserved for 24 hours at 80° C. for removing the impurities and natural oxide layers on the surface. The ultrasonic cleanings are repeated using deionized water. Drying is conducted.

(2) Preparing a Hyaluronic Acid-Alginic Acid Microsphere

At room temperature, 30 g of sodium hyaluronate and 30 g of sodium alginate are weighed separately, having a viscosity average molecular weight of 800 thousand Dalton. Both of them are put into the high speed vacuum homogenizer. 1000 ml of deionized water is added to dissolve them. Next, 100 ml of calcium chloride solution hailing a concentration of 3% is added. Vacuum homogenizing is conducted under the strong agitation. Then ethanol having three times volume than that of the mixture solution of the calcium chloride solution, the sodium hyaluronate and the sodium alginate is added. The agitation is continued to generate a deposit of the hyaluronic acid-alginic acid microspheres (that is the mould for preparing micropores). Washing is conducted three times using anhydrous ethanol. Freeze vacuum drying is conducted. Next, the microspheres are suspended in 1000 ml of anhydrous ethanol solution. A diameter of the hyaluronic acid-alginic acid microspheres is 5-10 um.

(3) Preparing a Titanium Sol Solution

At room temperature, 50 ml of tetrabutyl titanate is measured and dissolved in 1000 ml of anhydrous ethanol. Under the agitation, 100 ml of the 1% sodium alginate solution is slowly added. Next, 3 ml of acetylacetone is added. The agitation continues at the room temperature and the stable and uniform titanium sol solution is generated after 30 minutes. Aging is conducted at the room temperature for 24 hours.

(4) Coating and Pore-Forming

At room temperature, the aged titanium sol solution is mixed with the ethanol suspension of the hyaluronic acid-alginic acid microspheres having a volume the same as that of the aged titanium sol solution. The mixture is coated on the surface of the stapler (suturing device) titanium nail body using a salivation method. A thickness of the coating film is controlled to about 10-15 um.

The coated stapler (suturing device) titanium nails are dried at 90° C. Next, the stapler (suturing device) titanium nail are heat treated in hot water of 95° C. for 5 hours. With the hyaluronic acid and the alginic acid dissolved and stripped entirely in the hot water, a microporous titanium dioxide film having a pore diameter of 5-10 um, is generated on the surface of the coated titanium nails.

(5) Calcining

The coated stapler (suturing device) titanium nails are roasted in a calculator, with the temperature raised at a constant rate of 2° C./min. Heat preservation is conducted for 3 hours after the temperature reaches 500° C. The titanium nails are extracted after natural cooling, and a firm microporous titanium dioxide ceramic layer is generated on the surface of the stapler (suturing device) titanium nails. Washing in water and drying are conducted. A thickness of the ceramic layer is 5-10 um. The micropores are arranged uniformly, having a pore diameter of 0.5-6.5 um. Some micropores are connected with each other.

Embodiment 6

(1) Pretreating

Several (n) stapler (suturing device) titanium nails are ultrasonically cleaned in the deionized water to remove the surface attachments. The titanium nails are put into 1000 ml of NaOH solution having a concentration of 3.5 mol/L. The titanium nails are heat preserved for 24 hours at 80° C. for removing the impurities and natural oxide layers on the surface. The ultrasonic cleanings are repeated using deionized water. Drying is conducted.

(2) Preparing a Hyaluronic Acid-Alginic Acid Microsphere

At room temperature, 10 g of sodium hyaluronate and 10 g of sodium alginate are weighed separately, having a viscosity average molecular weight of 1500 thousand Dalton. Both of them are put into the high speed vacuum homogenizer. 1000 ml of deionized water is added to dissolve them. Next, 200 ml of calcium chloride solution having a concentration of 1% is added. Vacuum homogenizing is conducted under the strong agitation. Then ethanol having three times volume than that of the mixture solution of the calcium chloride solution, the sodium hyaluronate and the sodium alginate is added. The agitation is continued to generate a deposit of the hyaluronic acid-alginic acid microspheres (that is the mould for preparing micropores). Washing is conducted three times using anhydrous ethanol. Freeze vacuum drying is conducted. Next, the microspheres are suspended in the 1000 ml of anhydrous ethanol solution. A diameter of the hyaluronic acid-alginic acid microspheres is 5-10 um.

(3) Preparing a Titanium Sol Solution

At room temperature, 100 ml of tetrabutyl titanate is measured and dissolved in 1000 ml of anhydrous ethanol. Under the agitation, 200 ml of the 1% sodium alginate solution is slowly added. Next. 6 ml of acetylacetone is added. The agitation continues at room temperature and the stable and uniform titanium sol solution is generated after 30 minutes. Aging is conducted at the room temperature for 24 hours.

(4) Coating and Pore-Forming

At room temperature, the aged titanium sol solution is mixed with the ethanol suspension of the hyaluronic acid-alginic acid microspheres, having a volume the same as that of the aged titanium sol solution. The mixture is coated on the surface of the stapler (suturing device) titanium nail body using a salivation method. A thickness of the coating film is controlled to about 10-15 um.

The coated stapler (suturing device) titanium nails are dried at 90° C. Next, the stapler (suturing device) titanium nail are heat treated in the hot water of 98° C. for 5 hours. With the hyaluronic acid and the alginic acid dissolved and stripped entirely in the hot water, a microporous titanium dioxide film having a pore diameter of 5-10 um, is generated on the surface of the coated titanium nails (5) Calcining The stapler (suturing device) titanium nails are roasted in a calculator, with the temperature raised at a constant rate of 2° C./min. Heat preservation is conducted for 3 hours after the temperature reaches 500° C. The titanium nails are extracted after natural cooling, and a firm microporous titanium dioxide ceramic layer is generated on the surface of the stapler (suturing device) titanium nails. Washing in water and drying are conducted. A thickness of the ceramic layer is 5-10 um. The micropores are arranged uniformly, having a pore diameter of 0.5-6.5 um. Some micropores are connected with each other.

Embodiment 7

(1) Pretreating

Several (n) stapler (suturing device) titanium nails are ultrasonically cleaned in the deionized water to remove the surface attachments. The titanium nails are put into 1000 ml of NaOH solution that having a concentration of 5 mol/L. The titanium nails are heat preserved for 24 hours at 80° C. for removing the impurities and natural oxide layers on the surface. Then ultra sonic cleanings are repeated using deionized water. Drying is conducted.

(2) Preparing Hyaluronic Acid-Alginic Acid Microspheres

At room temperature, 10 g of sodium hyaluronate and 10 g of sodium alginate are weighed separately, having a viscosity average molecular weight of 1500 thousand Dalton. Both of them are put into the high speed vacuum homogenizer. 1000 ml of deionized water is added to dissolve them. Next, 200 ml of calcium chloride solution having a concentration of 1% is added. Vacuum homogenizing is conducted under the strong agitation. Then ethanol having three times volume than that of the mixture solution of the calcium chloride solution, the sodium hyaluronate and the sodium alginate is added. The agitation is continued to generate a deposit of the hyaluronic acid-alginic acid microspheres (that is the mould for preparing micropores). Washing is conducted three times using anhydrous ethanol. Freeze vacuum drying is conducted. Next, the microspheres are suspended in the 1000 ml of anhydrous ethanol solution. A diameter of the hyaluronic acid-alginic acid microspheres is 5-10 um.

(3) Preparing a Titanium Sol Solution

At room temperature, 50 ml of tetrabutyl titanate is measured and dissolved in 100 ml of anhydrous ethanol. Under the agitation, 100 ml of the 1% sodium alginate solution is slowly added. Next, 3 ml of acetylacetone is added. The agitation continues at the room temperature and the stable and uniform titanium sol solution is generated after 30 minutes. Aging is conducted at the room temperature for 24 hours.

(4) Coating and Pore-Forming

At room temperature, the aged titanium sol solution is mixed with the ethanol suspension of the hyaluronic acid-alginic acid microspheres having a volume the same as that of the aged titanium sol solution. The mixture is coated on the surface of the stapler (suturing device) titanium nail body using a salivation method. A thickness of the coating film is controlled to about 10-15 um.

The coated stapler (suturing device) titanium nails are dried at 90° C. Next, the stapler (suturing device) titanium nail are heat treated in the hot water of 95° C. for 5 hours. With the hyaluronic acid and the alginic acid dissolved and stripped entirely in the hot water, a macroporous titanium dioxide film having a pore diameter of 5-10 um, is generated on the surface of the coated titanium nails.

(5) Calcining

The coated stapler (suturing device) titan um nails are roasted in a calcinator, with the temperature raised at a constant rate of 2° C./min. Heat preservation is conducted for 3 hours after the temperature reaches 500° C. The titanium nails are extracted after natural cooling, and a firm microporous titanium dioxide ceramic layer is generated on the surface of the stapler (suturing device) titanium nails. Washing in water and drying are conducted. A thickness of the ceramic layer is 5-10 um. The micropores are arranged uniformly, having a pore diameter of 0.5-6.5 um. Some micropores are connected with each other Embodiment 8

(1) Pretreating

Several (n) stapler (suturing device) titanium nails are ultrasonically cleaned in the deionized water to remove the surface attachments. The titanium nails are put into 1000 ml of NaOH having a concentration of 5 mol/L. The titanium nails are heat preserved for 24 hours at 80° C. for removing the impurities and natural oxide layers on the surface. Then ultrasonic cleanings are repeated using deionized water. Drying is conducted.

(2) Preparing Hyaluronic Acid-Alginic Acid Microspheres

At room temperature, 10 g of sodium hyaluronate and 10 g of sodium alginate are weighed separately, having a viscosity average molecular weight of 1500 thousand Dalton. Both of them are put into the high speed vacuum homogenizer. 1000 ml of deionized water is added to dissolve them. Next, 200 ml of calcium chloride solution having a concentration of is added. Vacuum homogenizing is conducted under the strong agitation. Then ethanol having three times volume than that of the mixture solution of the calcium chloride solution, the sodium hyaluronate and the sodium alginate is added. The agitation is continued to generate a deposit of the hyaluronic acid-alginic acid microspheres (that is the mould for preparing micropores). Washing is conducted three times using anhydrous ethanol. Freeze vacuum drying is conducted. Next, the microspheres are suspended in the 1000 ml of anhydrous ethanol solution. A diameter of the hyaluronic acid-alginic acid microspheres is 5-10 um.

(3) Preparing a Titanium Sol Solution

At room temperature, 50 ml of tetrabutyl titanate is measured and dissolved in 1000 ml of anhydrous ethanol. Under the agitation, 100 ml of the 1% sodium alginate solution is slowly added. Next, 3 ml of acetylacetone is added. The agitation continues at the room temperature and the stable and uniform titanium sol solution is generated after 30 minutes. Aging is conducted at the room temperature for 24 hours.

(4) Coating and Pore-Forming

At room temperature, the aged titanium sol solution is mixed with the ethanol suspension of the hyaluronic acid-alginic acid microspheres, having a volume the same as that of the aged titanium sol solution. The mixture is coated on the surface of the stapler (suturing device) titanium nail body using a salivation method. A thickness of the coating film is controlled to about 10-15 um.

The coated stapler (suturing device) titanium nails are dried at 90° C. Next, the stapler (suturing device) titanium nail are heat treated in the hot water of 98° C. for 5 hours. With the hyaluronic acid and the alginic acid dissolved and stripped entirely in the hot water, a microporous titanium dioxide film having a pore diameter of 5-10 um, is generated on the surface of the coated titanium nails.

(5) Calcining

The coated stapler (suturing device) titanium nails are roasted in a calcinator, with the temperature raised at a constant rate of 2° C./min. Heat preservation is conducted for 5 hours after the temperature reaches 300° C. The titanium nails are extracted after natural cooling, and a firm microporous titanium dioxide ceramic layer is generated on the surface of the stapler (suturing device) titanium nails. Washing in water and drying are conducted. A thickness of the ceramic layer is 5-10 um. The micropores are arranged uniformly, having a pore diameter of 0.5-6.5 um. Some micropores are connected with each other.

The titanium nails capable of loading a drug obtained above can be used to prepare the dung-loaded titanium nails by loading with a drug. The embodiments are provided as below:

Embodiment 1 of Loading a Drug

At room temperature, the stapler (suturing device) titanium nails capable of loading a drug are put in the vacuum device. An sulfadiazine solution or silver sulfadiazine solution having a concentration of 15% is imported under the vacuum. Then the titanium nails are extracted and put into an another vacuum device to be dried under vacuum, so as to obtain drug-loaded stapler (suturing device) titanium nails loaded with the sulfadiazine or silver sulfadiazine.

Embodiment 2 of Loading a Drug

At room temperature, the stapler (suturing device) titanium nails capable of loading a drug are put in the vacuum device. A growth factor ether solution having a concentration of 15% is imported under the vacuum. Then the titanium nails are extracted and put into another vacuum device to be dried under vacuum, so as to obtain drug-loaded stapler (suturing device) titanium nails loaded with a growth factor.

Embodiment 3 of Loading a Drug

At room temperature, the stapler (suturing device) titanium nails capable of loading a drug are put in the vacuum device. One of various growth promoting factors for human tissue cells, an epidermal growth factor solution having a concentration of 65% is imported under the vacuum. Then the titanium nails are extracted and put into the vacuum freeze dryer to be dried, so as to obtain drug-loaded stapler (suturing device) titanium nails loaded with the epidermal growth factor, which is one of various human tissue cell growth promoting factors.

The present invention utilizes the properties of the pure titanium, the titanium dioxide, the hyaluronic acid, and the alginic acid, to make surface treatments for the existing stapler (suturing device) titanium nails, so that the pure titanium, the titanium dioxide, the hyaluronic acid-alginic acid react with each other. The firm microporous titanium dioxide ceramic layer is generated on the surface of the stapler (suturing device) titanium nails. The micropores are arranged uniformly, having an average pore diameter of 0.5-6.5 um, to increase the surface area of the stapler (suturing device) titanium nails and work as a storage space for the drug when loading a drug. Further, the drug is stably and uniformly distributed in the micropores on the surface of the stapler (suturing device) titanium nails, slowly releasing the drug in tissues in a targeted manner, to play a role in bacteriostasis and promoting healing etc.

As to the titanium nails capable of loading a drug of the present invention. First, it facilitates loading the antibacterial drugs and the drugs for promoting healing, and has a slow-release function. Second, exfoliations are more difficult to generate from the surface of the titanium nails due to the ceramic's property of corrosion resistance thus overcoming the side effects caused after implanting the existing stapler (suturing device) titanium nails into the human body.

Of course, the present invention of the titanium nails capable of loading a drug and the preparation method thereof can also be used in other medical instruments that need titanium nails. They can also be used to prepare drug-loaded titanium nails loaded with other drugs according to clinical needs.

What is described above is just the preferred embodiments of the present invention, and does not limit the present invention in any form. The simple amendments, equivalent changes or modifications made by the ordinary skilled person in the art in view of the disclosed technical contents above, all fall within the protection scope of the invention.

The invention claimed is:

1. A preparation method of a titanium nail capable of loading a drug, wherein the titanium nail capable of loading the drug comprises a titanium nail body, and a microporous ceramic layer capable of loading the drug arranged on a surface of the titanium nail body; the preparation method of the titanium nail capable of loading the drug comprises:
   (1) pretreating the surface of the titanium nail body by a alkaline solution, repeatedly cleaning with deionized water to remove the alkaline solution from the titanium nail body and drying the titanium nail body;
   (2) preparing a hyaluronic acid-alginic acid microsphere:
      weighing equal amounts of sodium hyaluronate and sodium alginate and putting the sodium hyaluronate and the sodium alginate into a vacuum homogenizer,
      adding the deionized water and a calcium chloride solution sequentially, vacuum homogenizing under a agitation,
      adding ethanol and continuing to agitate to generate a deposit of the hyaluronic acid-alginic acid microsphere,
      washing the titanium nail body with anhydrous ethanol,
      vacuum freeze-drying the titanium nail body,
      suspending the titanium nail body in an anhydrous ethanol solution;
   (3) preparing titanium sol solution: dissolving tetrabutyl titanate in the ethanol; adding a sodium alginate solution and acetylacetone sequentially and agitating the titanium sol solutions; continuing to agitate to generate a stable and uniform titanium sol solution; and aging at a room temperature;
   (4) coating and pore-forming: mixing an ethanol suspension of the hyaluronic acid-alginic acid microsphere obtained from step (2) with the titanium sol solution obtained from step (3) to obtain a mixed solution,
      coating the surface of the titanium nail body with the mixed solution and drying to obtain a coated titanium nail, heat treating the coated titanium nail in water,
      with both the hyaluronic acid and the alginic acid dissolving and stripping in the water, forming a microporous titanium dioxide film on a surface of the coated titanium nail; and
   (5) calcining: calcining the titanium nail coated with the microporous titanium dioxide film obtained from step (4) in a calcinator to form the titanium nail having a rutile type microporous titanium dioxide ceramic layer,
      water washing and drying to obtain the titanium nail capable of loading the drug.

2. The preparation method of the titanium nail capable of loading the drug of claim 1, wherein step (2) includes:
   weighing with equal amounts of 10-30 g of the sodium hyaluronate and the sodium alginate and putting the sodium hyaluronate and the sodium alginate into the vacuum homogenizer,
   adding the deionized water to dissolve the sodium hyaluronate and the sodium alginate, adding 100-300 ml of the calcium chloride solution at a concentration of 1%-3% and vacuum homogenizing under the agitation,
   adding the ethanol with three times volume than that of a mixture solution of the calcium chloride solution, the sodium hyaluronate and the sodium alginate and agitating continually to generate the deposit of the hyaluronic acid-alginic acid microsphere,
   washing the titanium nail body three times using the anhydrous ethanol, vacuum freeze-drying the titanium nail body, and
suspending the titanium nail body in the anhydrous ethanol solution,
wherein a viscosity-average molecular weight of the sodium hyaluronate is 800-1500 thousand Dalton, and a diameter of the hyaluronic acid-alginic acid microsphere is 5-10 μm.

3. The preparation method of the titanium nail capable of loading the drug of claim 1, wherein step (3) includes:
measuring and dissolving 50-100 ml of the tetrabutyl titanate in 1000 ml of the anhydrous ethanol,
adding 100-200 ml of the 1% sodium alginate solution when agitating, adding 3-6 ml of acetylacetone, and
agitating continually at the room temperature to generate the titanium sol solution, and
aging at room temperature for 24 hours.

4. The preparation method of the titanium nail capable of loading the drug of claim 1, wherein step (4) includes:
mixing the ethanol suspension of the hyaluronic acid-alginic acid microsphere Obtained from step (2) with the titanium sol solution obtained from step (3) in a proportion of 2-4.5:3, and agitating to obtain the mixed solution,
coating the mixed solution on the surface of the titanium nail body using a method of casting method, wherein a thickness of a coating film is 10-15 um,
drying the titanium nail body at 90° C. to obtain the coated titanium nail,
heat treating the coated titanium nail in the water at 95-98° C.,
forming the microporous titanium dioxide film on the surface of the coated titanium nail by dissolving and stripping using hyaluronic acid and alginic acid in the water.

5. The preparation method of the titanium nail capable of loading the drug of claim 1,
wherein the heated alkaline solution in step (1) is NaOH solution having a temperature of 70-90° C., and a concentration of 2-5 mol/L,
wherein the titanium nail body is heat preserved for 24-48 hours in the NaOH solution,
wherein a calcining condition in the calcinator of step (5) is that the temperature is raised at a constant rate of 2° C./min, and heat preservation is conducted for 3-5 hours after the temperature reaches 300-500° C.

6. A titanium nail capable of loading a drug prepared by the preparation method of the titanium nail capable of loading the drug according to claim 1, wherein a plurality of micropores having an average pore diameter of 0.5-6.5 μm and connected with each other, are arranged uniformly in the rutile type macroporous titanium dioxide ceramic layer.

7. A preparation method of a drug-loaded titanium nail with the titanium nail capable of loading the drug according to claim 6, wherein the method includes:
putting the titanium nail capable of loading a drug into a vacuum device;
importing the drug to be loaded,
dissolving the drug in a volatile organic solvent under vacuum conditions;
extracting the titanium nail; and
putting the titanium nail into another vacuum device to be dried under vacuum.

8. A drug-loaded titanium nail prepared by the preparation method of the drug-loaded titanium nail according to claim 7, wherein the drug-loaded titanium nail is a drug-loaded titanium nail loaded with a material selected from a group consisting of sulfadiazine, silver sulfadiazine, and a drug-loaded titanium nail loaded with a growth factor.

9. A preparation method of a drug-loaded titanium nail with the titanium nail capable of loading the drug according to claim 6, wherein the method includes:
putting the titanium nail capable of loading a drug in a vacuum device;
importing a solution of the drug to be loaded in a vacuum condition;
extracting the titanium nail and putting the titanium nail into a vacuum freeze-dryer to be dried.

10. A drug-loaded titanium nail prepared by the preparation method of the drug-loaded titanium nail according to claim 9, wherein the drug-loaded titanium nail is a titanium nail loaded with various growth promoting factors for human tissue cells.

11. A titanium nail capable of loading a drug prepared by the preparation method of the titanium nail capable of loading the drug according to claim 2, wherein a plurality of micropores having an average pore diameter of 0.5-6.5 μm and connected with each other, are arranged uniformly in the ruffle type microporous titanium dioxide ceramic layer.

12. A titanium nail capable of loading a drug prepared by the preparation method of the titanium nail capable of loading the drug according to claim 3, wherein a plurality of micropores having an average pore diameter of 0.5-6.5 μm and connected with each other, are arranged uniformly in the rutile type microporous titanium dioxide ceramic layer.

13. A titanium nail capable of loading a drug prepared by the preparation method of the titanium nail capable of loading the drug according to claim 4, wherein a plurality of micropores having an average pore diameter of 0.5-6.5 μm and connected with each other, are arranged uniformly in the rutile type, microporous titanium dioxide ceramic layer.

14. A titanium nail capable of loading a drug prepared by the preparation method of the titanium nail capable of loading the drug according to claim 5, wherein a plurality of micropores having an average pore diameter of 0.5-6.5 μm and connected with each other, are arranged uniformly in the rutile type microporous titanium dioxide ceramic layer.

* * * * *